United States Patent
Byrne et al.

(10) Patent No.: US 9,456,734 B2
(45) Date of Patent: Oct. 4, 2016

(54) SCANNER FOR AN ENDOSCOPE

(75) Inventors: Christopher Gerard Byrne, Berwick (AU); Robert Alan Pattie, Nyora (AU)

(73) Assignee: OPTISCAN PTY LTD, Notting Hill, Victoria (AU)

( * ) Notice: Subject to any disclaimer, the term of this patent is extended or adjusted under 35 U.S.C. 154(b) by 488 days.

(21) Appl. No.: 13/878,729

(22) PCT Filed: Oct. 12, 2011

(86) PCT No.: PCT/AU2011/001303
§ 371 (c)(1),
(2), (4) Date: Jun. 27, 2013

(87) PCT Pub. No.: WO2012/048374
PCT Pub. Date: Apr. 19, 2012

(65) Prior Publication Data
US 2013/0274597 A1 Oct. 17, 2013

(30) Foreign Application Priority Data
Oct. 12, 2010 (AU) ................................ 2010904552

(51) Int. Cl.
*A61B 1/06* (2006.01)
*A61B 1/00* (2006.01)
(Continued)

(52) U.S. Cl.
CPC ........... *A61B 1/00165* (2013.01); *A61B 1/005* (2013.01); *A61B 1/00096* (2013.01);
(Continued)

(58) Field of Classification Search
CPC .......... A61B 1/00096; A61B 1/00172; A61B 1/00165; G02B 23/2469; G02B 23/2476; G02B 26/103
USPC ............... 600/425, 182, 478, 143, 127, 129; 359/205.1
See application file for complete search history.

(56) References Cited

U.S. PATENT DOCUMENTS

| 6,608,684 B1 | 8/2003 | Gelikonov et al. |
| 6,950,692 B2 | 9/2005 | Gelikonov et al. |

(Continued)

FOREIGN PATENT DOCUMENTS

| JP | 61-250608 | 11/1986 |
| JP | 2001-079007 | 3/2001 |

(Continued)

OTHER PUBLICATIONS

JPS61250608 Machine Translation from Google Translate with cover page (5 pages).*

(Continued)

*Primary Examiner* — Anhtuan T Nguyen
*Assistant Examiner* — Timothy J Neal
(74) *Attorney, Agent, or Firm* — Honigman Miller Schwartz and Cohn LLP; Andrew N. Weber; Jonathan P. O'Brien

(57) ABSTRACT

A scanner for an endoscope comprising:
  a scanning mechanism comprising a light transmitter and arranged to move the light transmitter to perform a scan;
  a lens system arranged to optically couple the light transmitter to a target during a scan;
  a first housing which houses at least a first portion of the lens system;
  a second housing which houses at least the fiber scanning mechanism; and
  a bendable joint joining the first and second housings such that in a scanning configuration the bendable joint joins the first and second housings so that optical elements in the first and second housings are aligned at a working separation, the bendable joint arranged to bend in response to insertion forces applied to the scanner during insertion of the scanner and revert to the scanning configuration in the absence of insertion forces.

15 Claims, 3 Drawing Sheets

(51) Int. Cl.
    *G02B 23/24*     (2006.01)
    *A61B 1/005*     (2006.01)
    *G02B 26/10*     (2006.01)
    *A61B 5/05*     (2006.01)
    *A61B 5/00*     (2006.01)

(52) U.S. Cl.
    CPC ....... *A61B1/00117* (2013.01); *A61B 1/00172* (2013.01); *G02B 23/2469* (2013.01); *G02B 23/2476* (2013.01); *G02B 26/103* (2013.01); *A61B 5/0066* (2013.01); *A61B 5/0068* (2013.01); *A61B 5/0084* (2013.01)

(56) References Cited

U.S. PATENT DOCUMENTS

| | | | |
|---|---|---|---|
| 7,435,217 B2 | 10/2008 | Wiklof | |
| 8,212,884 B2 | 7/2012 | Seibel et al. | |
| 8,258,457 B2 | 9/2012 | Kobayashi | |
| 2007/0167804 A1* | 7/2007 | Park et al. | .................... 600/459 |
| 2007/0249908 A1 | 10/2007 | Lu et al. | |
| 2008/0132834 A1* | 6/2008 | Melville | .................... 604/95.04 |
| 2009/0001589 A1 | 1/2009 | Joo | |
| 2010/0177368 A1 | 7/2010 | Kobayashi | |
| 2010/0204546 A1 | 8/2010 | Hassidov et al. | |

FOREIGN PATENT DOCUMENTS

| | | |
|---|---|---|
| WO | 2004/040267 | 5/2004 |
| WO | WO2006004743 | 4/2007 |

OTHER PUBLICATIONS

International Search Report for PCT/AU2011/001303 dated Jan. 12, 2012.

* cited by examiner

SCANNER FOR AN ENDOSCOPE

CROSS REFERENCE TO RELATED APPLICATION

This U.S. patent application claims the benefit of PCT application no. PCT/AU2011/001303, filed on Oct. 12, 2011, which claims priority to Australia Application No. 2010904552, filed on Oct. 12, 2010. The entire contents of the aforementioned applications are incorporated herein by reference in their entireties.

FIELD

The invention relates to a flexible scanner suitable for probe based endomicroscopy

BACKGROUND

The field of endomicroscopy has emerged over the past decade with several innovations enabling microscopic imaging of living tissues of humans and animals and other subjects without the previously required removal of tissue for physical sectioning into thin slices for examination under a bench microscope.

Various forms of optical sectioning microscopy have featured, including laser scanning confocal microscopy (us, MKT), multiphoton microscopy and other forms of non-linear scanning microscopy.

Clinical evidence has amassed as to the clinical benefit of endomicroscopy, including increased sensitivity and specificity of disease detection and, if used to select sites for traditional biopsy sampling, achievement of higher diagnostic yield from a reduced number of biopsy sampling sites.

The most established systems in practical clinical use have been used most in gastroenterological endoscopy (GI endoscopy) and involve two main technical approaches to miniaturization of the confocal microscope sufficient for endoscopic use. Both these approaches involve the use of optical fibre technology to provide a flexible conduit that separates bulky laser source and detection components from the imaging components near the tissue.

Of the two commercially available instruments, the first uses a single optical fibre acting as both an illumination and detection aperture, and the fibre is physically scanned in a raster pattern and this occurs within the distal end of the device. A miniature objective lens couples the plane traversed by the scanning fibre tip to an objective imaging plane at or beneath the surface of the tissue in front of the device. This lens is used bidirectionally, forward coupling the illumination source from fibre to sample, and then collecting fluorescent or reflected light from the focal plane and projecting it back into the source optical fibre form transmission back to the proximal detection unit. A contact window at the tip of the device in front of said lens provides a reference plane of tissue contact, and an actuation mechanism included in the imaging head moves the focal plane of the optical system to different distances beyond the contact window (thus effecting optical sectioning at dynamically variable depth relative to the surface of the tissue contacting the window), either by moving part of the optical system to shift the focal plane, or by moving the whole scanning mechanism and lens system relative to the window. This has resulted in devices that yield subcellular, sub-micron resolution across a usable sub-millimeter field of view, with dynamic adjustment of imaging depth under control of the endoscopist.

Commercially available scanners exploiting this approach have reached dimensions of 5 mm×43 mm as a rigid tip connected via a flexible umbilicus for integration with flexible and rigid endoscope devices. This is sufficiently small to allow integration into a modified gastrointestinal (GI) endoscope or surgical endoscope, the former requiring a slight rigidisation of a short length of the distal region of the endoscope to accommodate the rigid scanner components.

Variations on this approach have been proposed which include alternative scanning patterns (spiral fibre scanning, elliptical fibre scanning, lissajous pattern fibre scanning, and MEMS based mirror scanning) but at the dimensions required for endoscopy, none have yet been reported to produce the imaging performance or mechanical viability of the above approach.

The other of the commercially available instruments involves proximal scanning of a coherent imaging bundle of optical fibres, each acting in turn as a confocal illumination and detection aperture, sequentially. This approach removes the requirement for several of the moving parts required in the scanning fibre approach, and has facilitated more extreme miniaturization than the scanning fibre approach to date, allowing probes less than 3 mm diameter down to sub millimeter devices. This comes at the expense of resolution, being limited by the packing density of fibres (which cannot approach the resel density of a continuously moving fibre core), and devices in use have a maximum fibre count of 30,000 elements at the larger diameters down to less than 10,000 pixels for the smaller devices (compared to a 1024× 1024 pixels, or 1 megapixel, associated with the scanned fibre devices). These devices also do not allow the dynamic adjustment of imaging depth, although lens systems have been developed which fix individual devices at specific imaging depths, which may be at or beneath the tissue surface (see MKT specifications). The great advantage of these probes is that they are small enough, and have a sufficiently short rigid length at the tip, and are sufficiently flexible in between, to allow insertion through working channels of existing endoscopes without modification or integration.

To date, this has not been possible with the scanning fibre devices, due in part to diameter, but mostly to the rigid length resulting in the longitudinal arrangement of window, then objective lens, then fibre scanning region, fibre mount, and depth actuation mechanism.

Although further miniaturization of the scanned fibre approach has been demonstrated, the rigid length of the scanner, while shortened, still precludes insertion via working channels of unmodified GI endoscopes and still require integration into the endoscope. Sufficient further shortening of the rigid length of said scanner designs is limited little by the ability to make smaller components but fundamentally by the physics dictating the required longitudinal arrangements. Although the diameter of the components in the above have approached the diameter required for insertion into flexible endoscope working channels, the rigid length remains too long to navigate the bends in the device, including the permanently angled insertion port typically configured to ensure that if a device can be inserted into the first part of the channel, it will subsequently be able to negotiate any path through the endoscope in normal use.

SUMMARY

The invention provides a scanner for an endoscope comprising:

a scanning mechanism comprising a light transmitter and arranged to move the light transmitter to perform a scan;

a lens system arranged to optically couple the light transmitter to a target during a scan;

a first housing which houses at least a first portion of the lens system;

a second housing which houses at least the fibre scanning mechanism; and a bendable joint joining the first and second housings such that in a scanning configuration the bendable joint joins the first and second housings so that optical elements in the first and second housings are aligned at a working separation, the bendable joint arranged to bend in response to insertion forces applied to the scanner during insertion of the scanner and revert to the scanning configuration in the absence of insertion forces.

In an embodiment, the bendable joint is sufficiently rigid so as not to compress when the first housing is pressed against a surface during a scan.

In an embodiment, a second portion of the lens system is housed in the second housing.

In an embodiment, the lens system is housed in the first housing.

In an embodiment, the scanner comprises a third housing which houses a second portion of the lens system, and an additional bendable joint intermediate the first and third housings In an embodiment, the flexible optical transmitter comprises an optical fibre or a bundle of optical fibres.

The invention also provides a probe for an endoscope comprising a scanner as described above and a flexible umbilicus carrying the light transmitter and adapted to connect the scanner mechanism to a host system.

Thus, embodiments of the present invention enables the components of a scanned fibre scanner to be transiently flexed to allow insertion through the working channel, and then conform to a linear configuration once at the distal for apposition to, and imaging of, the tissue in front of the distal tip of the endoscope.

Advantageously, the embodiments enable sufficient miniaturisation and flexibility of a fibre scanning type scanner to allow insertion into common endoscope working channels regardless of make, thus enabling true fibre scanning and associated resolution and field of view comparable integrated approaches and far exceeding the resolution compromises of fibre bundle approaches previously used to access endoscope working channels and provision of features such as variable resolution and hardware (scan) zoom that are not achievable with fibre bundle approaches.

BRIEF DESCRIPTION OF THE DRAWINGS

Embodiments of the invention are described in connection with the following drawings in which.

DETAILED DESCRIPTION

Figure 1:
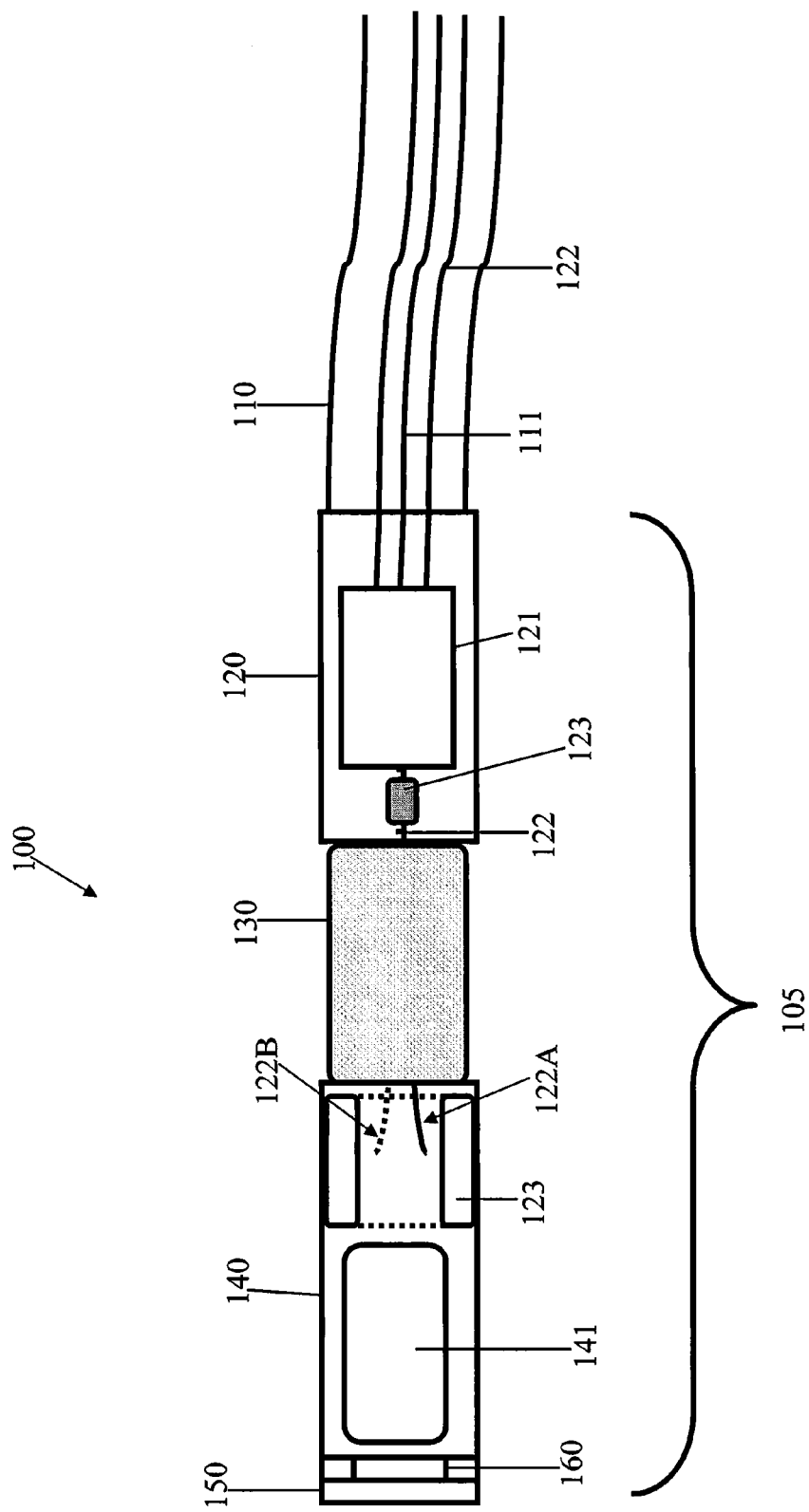
FIG. 1 is a schematic diagram of a scanner for an endoscope of a first embodiment.

FIG. 1 shows a probe 100 for a confocal endoscope. The probe has a flexible umbilicus 110 of dimensions suitable for insertion through the working channel of an endoscope (e.g. 3.3 mm diameter tubing) containing a flexible optical transmitter in the form of an optical fibre the optical fibre 122 and electrical conduits 111 to connect the scanner proximally to a host system (not shown) containing laser illumination, detection, scan control, and image display and acquisition components. In other embodiments, the flexible optical transmitter may be in the form of a bundle of optical fibres.

The distal end of the flexible umbilicus 110 is connected to a scanner 105. The scanner has a first short (typically <13 mm) rigid tube 140 that provides a housing for a confocal projection/objective lens system 141 positioned at a prescribed distance behind an outer tissue contact window 150 that seals the tip of the tube 140.

The inner region of this more distal short rigid tube 140 includes a protective bush 123 around the tip of the optical fibre 122 fabricated of a material that provides impact protection should the tip of the fibre contact the wall when scanning due to mechanical impact external to the scanner or bending during insertion into or withdrawal from the endoscope working channel. In other embodiments, protection may be provided by a coating material rather than bush 123.

A second short (typically <13 mm) rigid tube 120 provides a housing for a distal fibre scanning mechanism and is mounted onto the distal end of the above flexible umbilical tube 110.

The dimensions of each of the two short sections of tube are chosen to fall within the limits of length versus diameter for the target channel through which the device is to be inserted and withdrawn. Example dimensions are set out in Table 1.

TABLE 1

| Scanner Diameter | 3.8 mm Channel | 4.2 mm Channel |
| --- | --- | --- |
| 3 mm | 19 mm Rigid length | 21 mm Rigid Length |
| 3.5 mm | 17 mm Rigid Length | 18.5 mm Rigid Length |
| 4 mm | — | 16 mm Rigid Length |

Any suitable fibre scanning mechanism can be employed. In the embodiment, the scanning mechanism comprises a magnet 123, a fibre 122, and a fibre scanning mount and coils deployed within scanning mechanism housing 121. Examples of fibre scanning mechanism are described in WO 2004/040267 and US 2009/001589, the disclosures of which are incorporated herein by reference. In FIG. 1, the fibre is shown as moving between different scanning positions 122A, 122B.

A bendable joint 130 between the two housing sections is provided by section of flexible sprung tubing 130 that joins the first short rigid tube 140 to the second short rigid tube 120 such that the fibre 122 is positioned at a working separation corresponding to the required distance from the projection/objective lens 141.

The entry into the endoscope through which a probe is introduced has "gate" port with a bend in it so as to prevent the insertion of probes which do not bend sufficiently and hence are at risk of breaking during insertion. Typically, the bend is 135 degrees.

The bendable joint 130 has properties that will allow it to bend sideways when a lateral force is exerted, thus allowing the two short sections to follow through a curved channel (such as the gate port) but then to "snap" back into co-axial alignment within a sufficiently small tolerance to restore the functional alignment of the optical components (that is to return to a scanning configuration where the optical elements are positioned relative to the desired optical axis at a separation where they will still work). In the embodiment of FIG. 1, a working separation is maintained between the scanning fibre 122 to the scanning image plane of the projection/objective lens 141. The bendable joint may take a number of different forms. For example, a spring of closed configuration, with the wire cross section either cylindrical, flattened, rectangular or square. The spring is selected so as to allow small movements from straight to bent based on typical insertion forces applied to push devices through endoscope working channels. The spring of FIG. 1 is a closed stack construction that is not compressible when straight by the forces normally needed to locate the window of the scanner against the surface of a target (such as tissue to be examined), but rather opens out to permit lateral flexing. This design can provide reliable return to a precise axial and lateral alignment of scanner components after flexing.

An advantage of the spring being not compressible in its re-aligned state is that it can withstand being pushed against the tissue without inducing any bends in the scanner.

In other embodiments, the bendable joint 130 may take the form of non-kinking flexible tubes such as shape memory alloy tubular structures. In some embodiments, the shape memory material may be subject to electrical actuation to move between "bendable" and "rigid" states for insertion and imaging (scanning) phases of use, respectively.

The bendable joint 130 of the scanner 105 is coated with an appropriately flexible glue or covered with an a rubber or plastic tube so as to seal this section from ingress of fluid, and to provide a surface suitable for disinfection or sterilization.

No active imaging depth adjustment is included in the present invention. However, a passive mechanism for adjusting imaging depth is provided may be constructed by inclusion of an short flexible walled region 160 in the distal short rigid tube between the fixture of the projection/objective lens 141 and the fixture of the imaging window 150. The compression spring constants of this material are selected so as allow the imaging window 150 to move a useful distance (axially to the device), thus effecting a manual imaging depth adjustment controlled by the pressure applied to the device in positioning it against the tissue. This allows quite intuitive adjustment of the observed image from the surface of the tissue (light touch of probe to tissue) through to the deepest tissue imaging afforded by tissue scattering (typical for confocal endomicroscopy) with firm pressure on the tissue.

Figure 3:
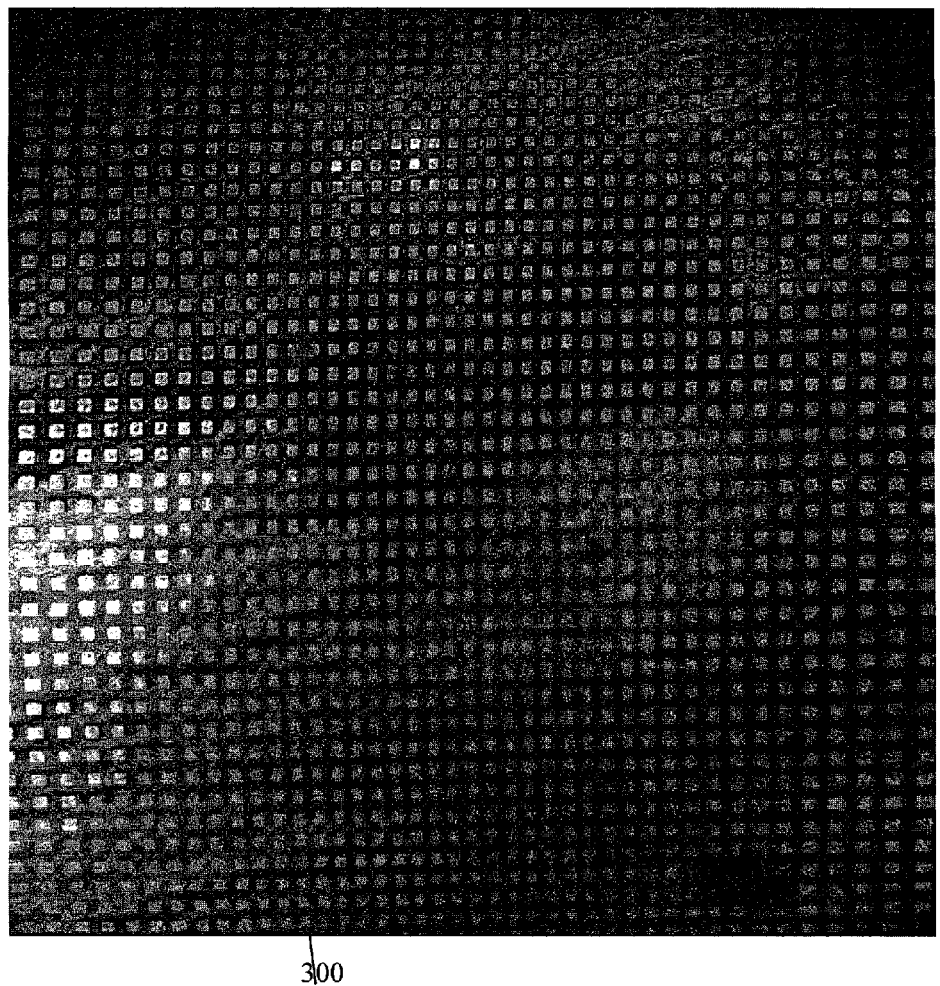
FIG. 3 is an exemplary image of a fluorescent grid collected with the endoscope of FIG. 1.

FIG. 3 shows an example of a fluorescent grid collected with a scanner made in accordance with the first embodiment.

Figure 2:
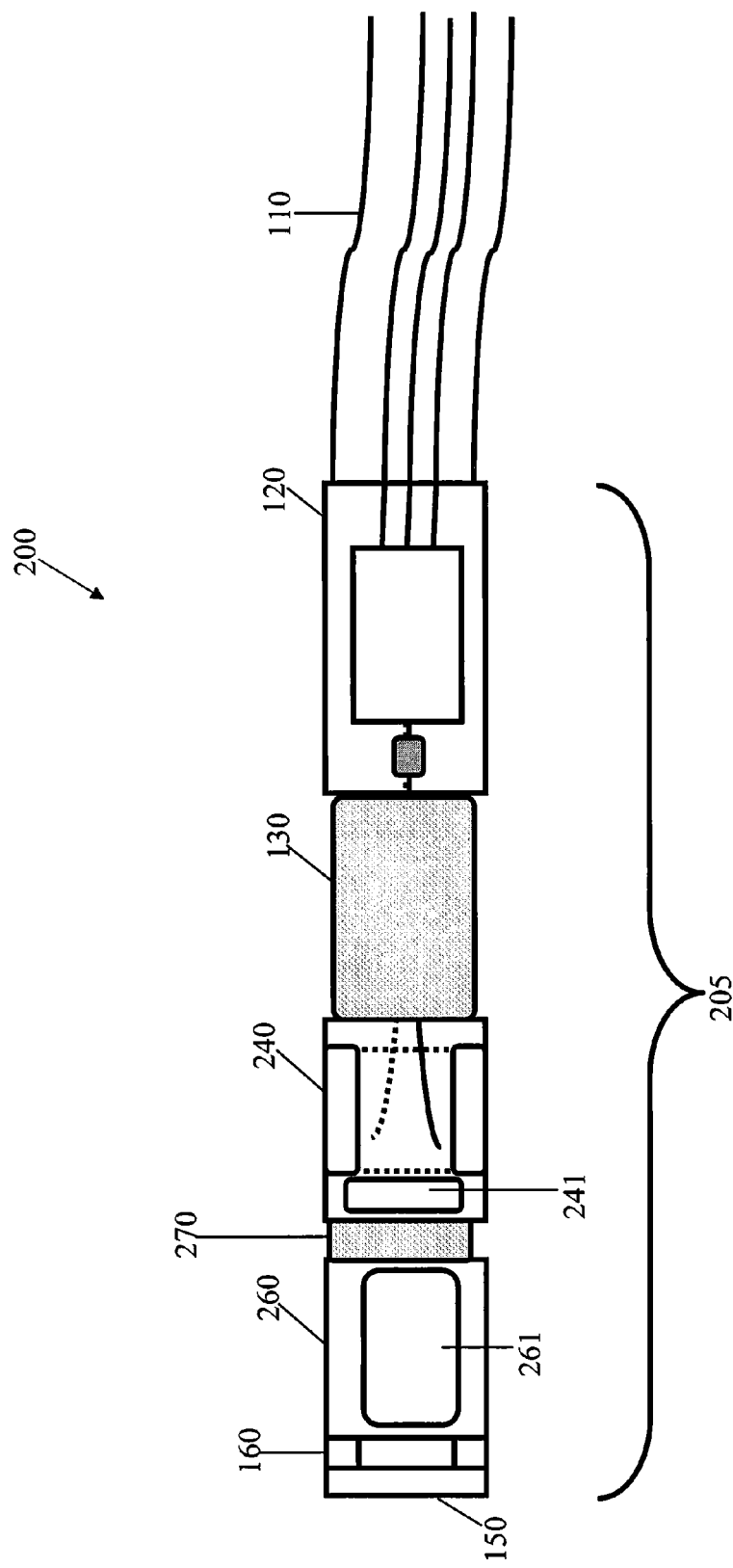
FIG. 2 is a schematic diagram of a scanner for an endoscope of a second embodiment.

FIG. 2 shows a probe 200 of a second embodiment with a different scanner 205 configuration. In this embodiment, there are three housings 120, 240, 260 joined by two bendable joints 130, 270. One of the bendable joints 270 is disposed between a first part 241 and a second part 261 of the lens system.

Persons skilled in the art will appreciate that in some embodiments, it is possible to modify the embodiment of FIG. 1 along the lines of FIG. 2 to provide a scanner with two housings where one part of the lens system is in the same housing as the scanning mechanism and another part of the lens system is in a separate housing.

Persons skilled in the art will appreciate that the scanner can be employed in microscope, an endoscope, an endomicroscope, an optical coherence tomograph, a confocal microscope, or a confocal multiphoton microscope or other image apparatus.

It will be understood to persons skilled in the art of the invention that many modifications may be made without departing from the spirit and scope of the invention, in particular it will be apparent that certain features of embodiments of the invention can be employed to form further embodiments.

It is to be understood that, if any prior art is referred to herein, such reference does not constitute an admission that the prior art forms a part of the common general knowledge in the art in any country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A scanner for an endoscope comprising:
    a scanning mechanism comprising a light transmitter and arranged to move the light transmitter to perform a scan;
    a lens system arranged to optically couple the light transmitter to a target during a scan;
    a first housing which houses at least a first portion of the lens system;
    a second housing which houses at least the scanning mechanism; and
    a bendable joint joining the first and second housings such that in a scanning configuration the bendable joint joins the first and second housings so that the lens system and the light transmitter are aligned at a working separation, the bendable joint arranged to bend in response to insertion forces applied to the scanner during insertion of the scanner and revert to the scanning configuration in the absence of insertion forces.

2. The scanner of claim 1, wherein the bendable joint is sufficiently rigid so as not to compress when the first housing is pressed against a surface during a scan, thereby preserving the working separation of the optical elements in the first and second housings.

3. The scanner of claim 1, wherein a second portion of the lens system is housed in the second housing.

4. The scanner of claim 1, wherein the lens system is housed in the first housing.

5. The scanner of claim 1, comprising a third housing which houses a second portion of the lens system and is located distally relative to the first housing, and an additional bendable joint intermediate the first and third housings.

6. The scanner of claim 1, wherein the flexible optical transmitter comprises an optical fibre or a bundle of optical fibres.

7. A probe for an endoscope comprising:
    a scanner as claimed in claim 1, and a flexible umbilicus carrying the light transmitter and adapted to connect the scanner mechanism to a host system.

8. An microscope, an endoscope, an endomicroscope, an optical coherence tomograph, a confocal microscope, or a confocal multiphoton microscope comprising the scanner of claim 1.

9. An imaging apparatus comprising the scanner of claim 1.

10. The scanner of claim 1, wherein the bendable joint is sufficiently rigid so as not to compress when the first housing is pressed against a surface during a scan, thereby preserving the working separation of the optical elements in the first and second housings, and a second portion of the lens system is housed in the second housing.

11. The scanner of claim 1, wherein the bendable joint is sufficiently rigid so as not to compress when the first housing is pressed against a surface during a scan, thereby preserving the working separation of the optical elements in the first and second housings, and the lens system is housed in the first housing.

12. The scanner of claim 5, wherein the bendable joint and the additional bendable joint are sufficiently rigid so as not to compress when the third housing is pressed against a surface during a scan, thereby preserving the working separation of the optical elements in the first and second housings and of the optical elements in the first and third housings.

13. The scanner of claim 12, wherein the flexible optical transmitter comprises an optical fibre or a bundle of optical fibres.

14. The scanner of claim 1, wherein the bendable joint is sufficiently rigid so as not to compress when the first housing is pressed against a surface during a scan, thereby preserving the working separation of the optical elements in the first and second housings, a second portion of the lens system is housed in the second housing, and the flexible optical transmitter comprises an optical fibre or a bundle of optical fibres.

15. The scanner of claim 1, wherein the bendable joint is sufficiently rigid so as not to compress when the first housing is pressed against a surface during a scan, thereby preserving the working separation of the optical elements in the first and second housings, the lens system is housed in the first housing, and the flexible optical transmitter comprises an optical fibre or a bundle of optical fibres.

* * * * *